United States Patent [19]
Augustine

[11] Patent Number: 5,638,813
[45] Date of Patent: Jun. 17, 1997

[54] TRACHEAL TUBE WITH SELF-SUPPORTING TRACHEAL TUBE CUFF

[75] Inventor: Scott D. Augustine, Bloomington, Minn.

[73] Assignee: Augustine Medical, Inc., Eden Prairie, Minn.

[21] Appl. No.: 476,485

[22] Filed: Jun. 7, 1995

[51] Int. Cl.⁶ .................................................. A61M 16/00
[52] U.S. Cl. .................................. 128/207.15; 604/96
[58] Field of Search ................... 128/207.14, 207.15, 128/207.18, 207.16; 604/96

[56] References Cited

U.S. PATENT DOCUMENTS

| | | | |
|---|---|---|---|
| 3,460,541 | 8/1969 | Doherty | 128/207.15 |
| 3,481,339 | 12/1969 | Puig | 128/207.15 |
| 3,504,676 | 4/1970 | Lomholt | 128/207.15 |
| 3,565,079 | 2/1971 | Jackson | 128/207.15 |
| 3,616,799 | 11/1971 | Sparks | 128/207.15 |
| 3,638,655 | 2/1972 | Doherty | 128/207.15 |
| 3,640,282 | 2/1972 | Kamen et al. | 128/207.15 |
| 3,659,611 | 5/1972 | Miller | 128/207.15 |
| 3,707,151 | 12/1972 | Jackson | 128/207.15 |
| 3,709,227 | 1/1973 | Hayward | 128/207.15 |
| 3,769,983 | 11/1973 | Merav | 128/207.15 |
| 3,799,173 | 3/1974 | Kamen | 128/207.15 |
| 4,013,097 | 3/1977 | Calandra | 128/207.15 X |
| 4,278,081 | 7/1981 | Jones | 128/207.15 |
| 4,495,948 | 1/1985 | Shapiro | 128/207.15 |
| 4,791,923 | 12/1988 | Shapiro | 125/207.15 |
| 4,979,505 | 12/1990 | Cox | 128/207.15 |
| 5,176,638 | 1/1993 | Don Michael | 604/101 |
| 5,285,777 | 2/1994 | Beckwith | 128/207.15 |
| 5,305,740 | 4/1994 | Kolobow | 128/207.14 |
| 5,322,062 | 6/1994 | Servas | 128/207.14 |

FOREIGN PATENT DOCUMENTS

| 0072230 | 7/1983 | European Pat. Off. . |
| 1113484 | 5/1968 | United Kingdom . |

OTHER PUBLICATIONS

Jack Kamen and Carolyn Wilkinson, "A New Low-pressure Cuff for Endotracheal Tubes", Anesthesiology, May 1971, pp. 482–485.

Dow Corning Bulletin 51–067, "SILASTIC Brand Endotracheal Tube", Oct. 1971.

*Primary Examiner*—V. Millin
*Assistant Examiner*—Eric P. Raciti
*Attorney, Agent, or Firm*—Baker, Maxham, Jester & Meador

[57] ABSTRACT

An endotracheal or tracheostomy tube with a self-inflating cuff near its distal end includes one or more resilient, compressible support parts within the cuff for exerting a low sealing pressure against a trachea during expiration.

21 Claims, 8 Drawing Sheets

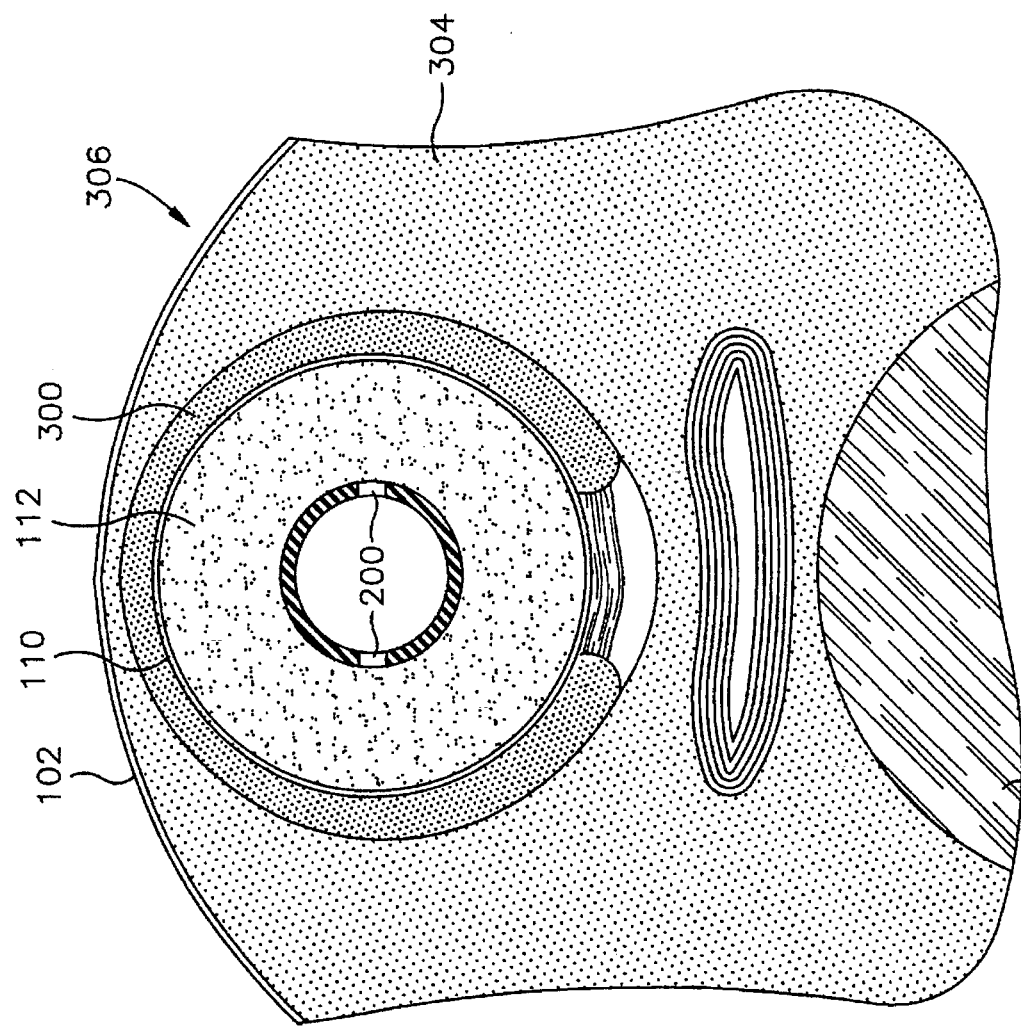
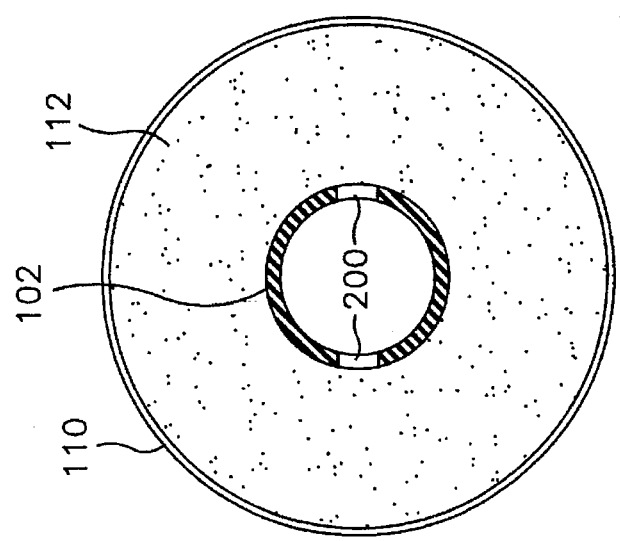
FIG. 3A
FIG. 3

TRACHEAL TUBE WITH SELF-SUPPORTING TRACHEAL TUBE CUFF

BACKGROUND OF THE INVENTION

The invention concerns endotracheal and tracheostomy tubes with inflatable cuffs.

When ventilatory support or protection of the airway is indicated, tracheal tubes have been the device of choice. The traditional tracheal tube ("breathing tube", "endotracheal tube" or "ETT") is placed into the patient's trachea through the mouth or nose to assist with breathing. It consists of a length of extruded, flexible PVC (or silicon rubber, or other rubber) tubing that has a connector on its proximal end to hook up to a ventilating means. Near the distal end is an inflatable, circumferential cuff or balloon that seals against the walls of the trachea when it is inflated. This seal between the cuff and tracheal wall allows positive pressure ventilation of the lungs and prevents vomited stomach contents from leaking down and soiling the lungs from above.

The alternative method of tracheal tube placement is through a tracheostomy (a surgical hole through the skin of the neck and directly into the trachea). This type of tracheal tube is called a "tracheostomy tube". The distal end and the inflatable cuff sealing means of both the tracheal and tracheostomy tubes are identical.

Tracheal tubes are the essential means of controlling the exchange of gases in the critically ill or surgical patient. The tracheal tube establishes a closed system whereby the gas pressure in the airway distal to the inflated cuff can be controlled, allowing external positive pressure mechanical ventilation of the patient's lungs.

The standard, currently used tracheal tubes have cuffs that resemble inflatable doughnuts near the distal end. The cuffs are usually made of a thin film of PVC or whatever material the tube is made of. The cuffs are manually inflated with pressurized air from a syringe through a small bore "pilot tube". The air is injected into the proximal end of the pilot tube, which is a thin piece of tubing for its proximal half and a small diameter channel molded into the side wall of the tracheal tube for its distal half. The pilot tube terminates at its distal end within the inflatable cuff of the tracheal tube. The pilot tube has a one-way valve at its proximal end to maintain pressure within the system.

To prevent the leakage of air from between the inflated cuff and the tracheal wall during mechanical ventilation, the pressure in the cuff must be equal to or greater than the peak inspiratory pressure within the airway. Peak inspiratory pressures are only achieved for 10%–25% of the ventilatory cycle but may be as high as 50 mm of mercury. Since the pressure within the standard cuff is static, the cuff pressure must be maintained at this relatively high pressure (equal to or greater than peak airway pressure) throughout the ventilatory cycle, to prevent leaks during the highest pressure portion of the cycle.

The cuffs containing relatively high static pressures transmit that same pressure to the adjacent tissue of the wall of the trachea. As cuff pressure exceeds the capillary blood pressure of the tracheal tissues, normally 25 mm of mercury, tissue ischemia or inadequate blood flow occurs. Prolonged ischemia can cause varying degrees of injury ranging from mild erosion of the mucosa, to destruction of the tracheal cartilage rings, to segmental tracheomalacia with dilation of the trachea. Even more dramatic is full thickness erosion which may result in perforation of the innominate artery anteriorly or perforation of the esophagus posteriorly. Late complications of tracheal stenosis, from mild to incapacitating obstruction are noted in the majority of patients requiring long term ventilatory support. Again, the problem is not with the pressure itself but rather that the pressure is applied in a static form for a prolonged period of time. Short term occlusion of blood flow does not damage most tissues but prolonged occlusion causes tissue ischemia and cell death.

During surgery the problem of excessive cuff pressures is exacerbated because the anesthetic gas nitrous oxide diffuses through the cuff material and into the cuff. The volume of gas within the cuff can more than double during an operation because of nitrous oxide diffusion. Obviously nitrous oxide diffusion into the cuff increases the pressure within the cuff and therefore the pressure against the tissue of the tracheal wall is also increased. This slowly increasing cuff pressure may not be detected by the clinician.

To prevent tissue damage caused by prolonged pressure from the cuff, doctors and nurses may periodically deflate and re-inflate the cuff. However, this procedure is rarely done frequently enough or for a long enough period of time to allow adequate reperfusion of the tissue. Therefore, this procedure does not dependably prevent tracheal wall ischemia. It is also a nuisance for the clinicians.

A variety of pressure regulating devices have been developed to attach to the pilot tube to regulate cuff pressure. These include pop-off valves, chambers and balloons to visualize the amount of pressure and automatic inflator/deflators. None of these devices have reliably solved the cuff pressure problem.

The second practical problem with the present tracheal tube and inflatable cuff design is that the pilot tube assembly and valve requires many parts with many connections, resulting in many chances for failure, more assembly time and higher manufacturing costs. Because the pilot tube and cuff are a closed, relatively high pressure system that must maintain its integrity for hours-to-days, any leaks or manufacturing defects will result in cuff deflation and failure of the tube. The need for high levels of quality control during the manufacturing process of this life supporting device obviously adds to the cost of the device. In addition to occasional manufacturing defects, leaks frequently develop during prolonged use, necessitating tube replacement. Tube replacement in a critically ill patient can itself be a life threatening procedure.

These many problems can be eliminated or at least minimized by abandoning the use of the traditional statically inflatable cuff as the sealing means. Clearly, there is a need for an improved sealing means for use with tracheal and tracheostomy tubes.

SUMMARY OF THE INVENTION

My invention includes tracheal tubes with an inflatable cuff. A tracheal tube according to the invention is made of a length of extruded, flexible tubing (preferably PVC plastic, but it could be another plastic, or silicon rubber, or other rubber, or metal), sized to fit within the human trachea. At the proximal end is a standard connector for connecting the tracheal tube to a breathing apparatus or ventilating means. Near the distal end is an inflatable, circumferential cuff or balloon that seals against the walls of the trachea when it is inflated. The cuff is made of a thin film of plastic or rubber, formed into an annular shape that surrounds the tube and that is sealed along its proximal and distal edges to the tube. The cuff and tube combination sealed at the cuffs' edges, creates an inflatable "doughnut" or bulbous annular sealing means.

My invention includes a combination of two parts that is not present in the standard tracheal tube and further dispenses with one standard part.

First, in my invention, the cuff, at rest, is held in an erected position by one or more compressible, resilient parts within the cuff which act between the tracheal tube and the cuff. Such parts may be, for example, compressible, annular foam plastic or foam rubber disks or washers surrounding the tube, within the cuff. These foam disks are preferably 0.18 to 0.5 inch thick and serve as supporting partitions within the cuff. At least one of the disks may be slightly larger in diameter than the largest human trachea for which the specific tube is sized and therefore will be radially compressed (without folding) when the tube is inserted into the patient's trachea. The compressed foam disk(s) create a static low pressure seal between the cuff and the tracheal wall, throughout the respiratory cycle.

Second, the cuff in my invention is self-inflating, to automatically increase the seal between the cuff and the trachea during the high pressure phase of ventilation. There are one or more holes or passageways communicating directly between the airway space where the distal end of the tube is located and the interior of the cuff. Preferably these holes pass through the wall of the tube communicating with the interior lumen. Alternately, these holes may pass through the cuff on its distal side, "downstream" in the trachea. These holes allow the higher pressure air, within the airway during the inspiratory phase of positive pressure ventilation, to flow into the cuff, expanding the cuff and increasing the seal against the tracheal wall. As the airway pressure decreases, decreasing the demand on the seal, the pressure within the cuff decreases simultaneously. Therefore, this design creates a dynamic high pressure seal corresponding with each respiratory cycle. During the low pressure phase of ventilation the seal is maintained only by the low pressure of the resilient parts. Because the resilient parts are only required to seal during the low pressure expiratory phase, these parts may be made from a light weight, low density, easily compressible and gently resilient foam. This very low pressure static seal against the tracheal wall allows normal blood flow in the tracheal tissues during the majority of the ventilatory cycle.

My design is absent a pilot tube and external means for cuff inflation or deflation. This significantly reduces the number of parts in the tube, simplifies assembly and reduces the number of airtight bonds that must have highly reliable quality control.

A principal objective of this invention is to provide a tracheal tube with an inflatable sealing member that creates a seal against the tracheal wall that is equal to or greater than the peak airway pressure during positive pressure ventilation (to prevent leakage of the inspiratory air pressure around the tube).

Importantly, the inflatable sealing member maintains at least a minimal static seal with the trachea throughout the respiratory cycle (to prevent soiling of the lungs with vomitus or blood from above).

A significant advantage of the tracheal tube of this invention is that the inflatable sealing member does not maintain high static pressures during the expiratory or low airway pressure phase of the ventilatory cycle (in order to allow tissue reperfusion). In this respect, the inflatable sealing member provides dynamically changing cuff pressures that correspond with the airway pressures that it is sealing against. Additionally, the inflatable sealing member will not over-inflate or allow diffusing nitrous oxide to be trapped in the cuff.

Significantly, the inflatable sealing member is easily and completely collapsible for easy and non-traumatic insertion through the vocal cords and trachea.

The tracheal tube of this invention is cheaper to manufacture and more dependable than the current standard tracheal tube with an inflatable cuff.

BRIEF DESCRIPTION OF THE DRAWINGS

FIG. 3 is a cross-sectional view through one foam disk (along III—III in FIG. 1), showing two of the passageways for communicating air pressure into the cuff.

FIG. 3A is a cross-sectional view through one foam disk when inserted into a patient's trachea.

Figures 1, 2:
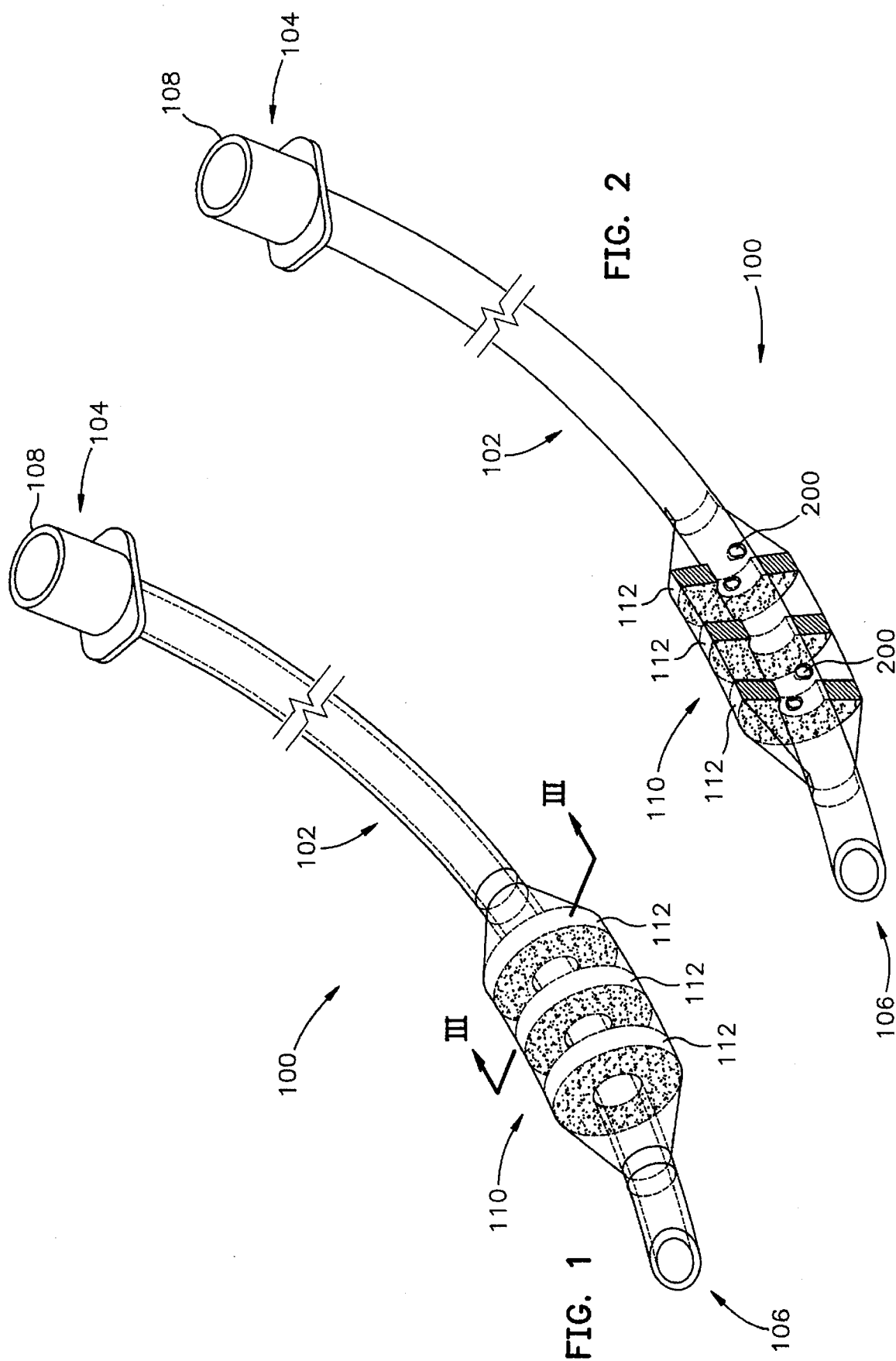
FIG. 1 is a perspective view of a first embodiment of the invention showing three foam disks, covering the holes in the tube from view. The cover overlaying the disks is transparent in this view.
FIG. 2 is a cut-away perspective view of the first embodiment.

DISCUSSION OF PRIOR ART a.) Self-inflating cuffs:

A variety of self-inflating cuffs or cuff-like structures tracheal and tracheostomy tubes are known in the prior art. These many designs exhibit varying degrees of effectiveness in creating a dependable seal during the high peak inspiratory pressure phase. Most of these designs fail to seal the airway during the low pressure phase. In order to overcome this deficiency, some include flap valves or a second inflatable cuff, in which case the sealing means is not dynamic.

U.K. #1,113,484 shows a self-inflating cuff communicating with holes through the wall of a tracheal tube. Additionally, there is a constriction of the bore of the tube to create a pressure gradient. The holes inflating the cuff are upstream of the constriction in the higher pressure zone.

U.S. Pat. No. 3,481,339 shows a dual cuff mechanism, one cuff within the other. The outer cuff is inflated through a pilot tube. The inner cuff is in communication with the inside of the tube and responds to airway pressure. The primary occlusion mechanism with this design is the externally-inflated cuff, therefore the problem of high static cuff pressures has not been overcome.

U.S. Pat. No. 3,460,541 shows a self-inflating cuff with an inflation aperture through the wall of the tube. Also includes a flap valve which covers the aperture preventing cuff deflation during the exhalation phase.

U.S. Pat. No. 3,504,676 shows a cuff mechanism including a pilot tube attached to a balloon which is within the airway and responds to airway pressure, increasing the cuff pressure in response to high airway pressures. The primary occlusion mechanism with this design is the cuff, therefore the problem of high static cuff pressure has not been overcome. Peak airway pressures are simply added to the static cuff pressures. Additionally, the time constant of the small bore pilot tube would not allow enough air to transfer fast enough, to respond to the rapid increase in airway pressure during inspiration.

U.S. Pat. No. 3,565,079 shows a self-inflating cuff design that "remains inflated during expiration therethrough." This is accomplished with two basic designs: 1. a series of slits or openings in the distal end of the cuff itself, open to the distal airway pressure; 2. a hole between the tube and the cuff to inflate the cuff during peak airway pressures and the hole is covered with a flap valve to prevent egress of the air, in each embodiment.

U.S. Pat. No. 3,707,151 shows a self-inflating cuff design where the interior of the cuff is in direct communication with the airway pressure within the tube. This patent mentions the need to maintain cuff inflation throughout the respiratory cycle and attempts to accomplish this with angled inflation passages and/or flap valves occluding the passages. At zero airway pressure and an unvalved communication passage, the cuff will deflate and lose the tracheal seal irrespective of the angle of the passageway. The flap valve version runs a high risk of trapping high, peak airway pressure air within the cuff and holding it there throughout the respiratory cycle.

Figure 9A:
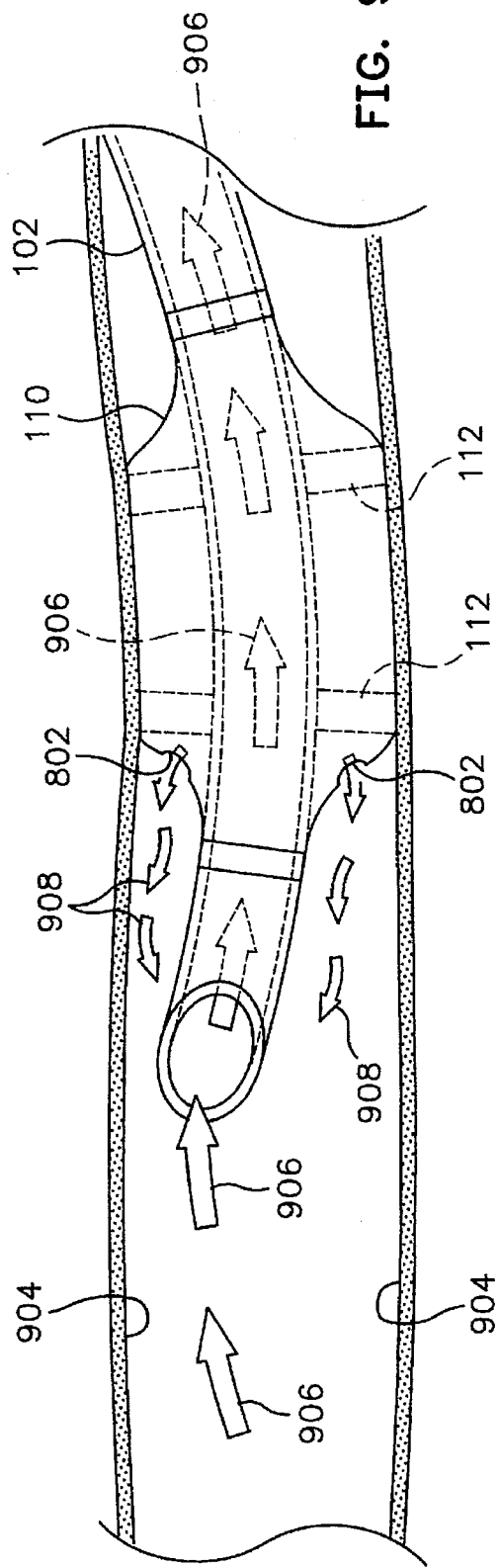
FIGS. 9A and 9B are side views of the fifth embodiment of the invention shown in FIG. 8. These diagrams show gas entering and exiting through the passageways, alternately inflating and deflating the cuff.

U.S. Pat. No. 4,278,081 shows a self-inflating tracheostomy cuff design where the interior of the cuff is in communication with the airway pressure. FIG. 9 clearly shows the collapse of the cuff during exhalation. As stated at Col 3, line 46; "In order to solve the problem of the inadvertent travel of stomach acids and like undesirable fluids from the stomach and esophagus to the trachea and lungs, an obturator is provided for insertion above the implantation point for the tracheal tube." The problem of leakage is solved by placing a plug into the stump end of the trachea above the tracheostomy site, external to the inflatable chamber.

U.S. Pat. No. 4,791,923 shows a dual cuff mechanism, one cuff within the other. The inner cuff is inflated through a pilot tube. The outer cuff is in communication with the inside of the tube by way of another pilot tube and responds to airway pressure. The primary occlusion mechanism with this design is the statically inflated cuff, therefore the problem of high static cuff pressures has not been overcome. Additionally, the time constant (rate of air movement) of the small bore pilot tube would not allow enough air to transfer into the cuff fast enough, to respond to the rapid increase in airway pressure during inspiration.

b.) Self-inflating skirts:

In order to solve some of the problems associated with the traditional cuffed tracheal tube, a number of skirt-like sealing means have been developed. In theory these are self-inflating during peak airway pressures.

U.S. 3,616,799 shows a skirt (not a cuff) that extends beyond the end of the tube with its open end facing downstream. The increased distal airway pressure is trapped within and expands the skirt outward into a seal with the trachea. The design includes an external "bead" (#16) or gasket that creates the seal throughout the respiratory cycle. The inventor recognizes that if the "bead" is resilient enough to reliably create a seal in the airway, it will also be very difficult to insert through the vocal cords and would probably apply considerable static pressure to the tracheal mucosa.

U.S. Pat. No. 3,709,227 shows an inflatable chamber which is specifically in communication with the airway pressure downstream, through passages directed into the downstream trachea rather than into the lumen of the tube. This patent teaches an additional "flexible annular lip", external to the inflatable chamber, to provide the seal with the trachea throughout the respiratory cycle. This lip would be very difficult to insert through the vocal cords.

U.S. Pat. No. 3,769,983 shows a self-inflating canopy-shaped skirt with an open distal end in communication with airway pressure. This device does not have an additional sealing means and the inventor notes, "At an instant of time the flow of air may be at a standstill... the canopy relaxes from its distended position receding from the surface lining." (Col 7, line 43). One problem with this device is that a significant portion of the respiratory cycle is close to zero airway pressure and this device does not occlude the airway during that period.

U.S. Pat. No. 4,979,505 shows two open ended parabolic skirts inverted to each other. The distal skirt is self-inflating in response to airway pressure. The distal skirt extends beyond the end of the tracheal tube and therefore must be self-supporting. No means are taught for holding the open end of the skirt in contact with the tracheal wall. Since the skirt would have to be purposefully oversized to accommodate a variety of tracheal sizes, the skirt would fold on itself in many cases and leak during the low pressure phase. These skirts would be very difficult to insert through the vocal cords.

c.) Disk-like flange sealing means:

A number of tracheal tubes have been developed with one or more disk-like flange sealing means. In these designs if the disks are stiff and resilient enough to create a dependable seal with the trachea, they will be difficult to insert past the vocal cords and will fold rather than compress. Folding of a disk will create leaks.

U.S. Pat. No. 3,659,611 shows one or more "thin, solid, resilient, disklike flanges," as the sealing means.

U.S. Pat. No. 5,305,740 shows a sealing means made of multiple "gill-collars" or "flange-collars". Each gill or flange is a thin ("eg 0.002 in"), soft, pliable ("eg plasticized vinyl sheet") element. Each gill has a collar portion to help attach it to the tube.

U.S. Pat. No. 5,322,062 shows a sealing means made of one or more thin, flexible, resilient annular disks each having a series of partial slits extending radially outward to the rim and be larger than the diameter of the airway.

d. Cellular foam filled cuffs:

A variety of foam filled cuffs have been developed in an attempt to create a low pressure seal with the trachea. The self-expanding, resilient bulbous foam sealing structure of these designs creates a gentle seal throughout the respiratory cycle. It has been recognized that added sealing pressure may be necessary at the time of peak airway pressures and some of these designs include self-inflating mechanisms to overcome this problem. The relatively large bulbous masses of foam described in each of these patents would not be easily compressible for insertion through the vocal cords and therefore the inventors have added a vacuum means to the inventions to forcibly collapse the bulbous foam sealing means during insertion.

U.S. Pat. No. 3,640,282 shows a tracheal tube with a foam filled cuff. The resilient foam within the cuff "preferably completely fills the cover 9 between the end portions 11 and 12 thereof", (Col. 3, line 55). It is recognized that this mass of foam would not passively compress during insertion. Therefore, the device incorporates a pilot tube to transmit a vacuum into the cuff, to cause it to forcibly collapse compressing the foam, for easy insertion into the trachea. The cuff does not communicate with the airway pressure. U.S. Pat. No. 3,799,173 shows a similar arrangement.

E.P. #0,072,230 (U.S. Pat. No. 4,495,948) shows a tracheal tube with a foam filled cuff. This mass of foam would not passively compress during insertion. Therefore, the device incorporates a pilot tube to transmit a vacuum into the cuff, to cause it to forcibly collapse compressing the foam, for easy insertion into the trachea, in all independent claims. Additionally, the pilot tube can communicate with the airway pressure through a fitting at the proximal end of the tube and is therefore intended to be a self-inflating design. However, the time constant of the small bore pilot tube would not allow enough air to transfer fast enough, to respond to the rapid increase in airway pressure during inspiration.

DETAILED DESCRIPTION OF THE PREFERRED EMBODIMENTS

Broadly, the present invention concerns an endotracheal or tracheostomy tube (hereinafter a "tracheal tube") with a distal end surrounded by a cuff that is resiliently upheld and selectively inflated in a novel way. Specifically, the inflatable cuff is self-inflating, under pressure provided by holes disposed in the tube or the cuff itself. Further, one or more resilient parts act between the outer surface of the tracheal tube and the cuff to maintain a minimal sealing pressure when the tracheal tube is inserted into a trachea.

FIG. 1 illustrates the various components of a first embodiment of a tracheal tube 100 in accordance with the invention. The tracheal tube 100 comprises a length of flexible tubing 102 and a proximal end 104 and a distal end 106. The flexible tubing 102 preferably comprises a length of extruded, flexible tubing such as PVC plastic, or another plastic, silicon rubber, or another sufficiently flexible material, sized to fit within the human trachea. The proximal end 104 of the tracheal tube 100 includes a connector to connect the tracheal tube 100 to a breathing apparatus or appropriate ventilator. If desired, the connector 108 may have a standard size, to conveniently mate with commercially available breathing equipment.

At the distal end 106 of the tracheal tube 100, an inflatable cuff 110 sheathes the flexible tubing 102. The cuff 110 comprises a flexible, inflatable, circumferential cuff or balloon that seals against the walls (not shown) of a trachea as discussed below. The cuff 110 is preferably made of a thin film of plastic, rubber or another flexible material, formed into an annular shape that sealably surrounds the flexible tubing 102. More particularly, the cuff 110 is sealed along its proximal and distal edges to the flexible tubing 102. The combination of the cuff 110 creates an inflatable "doughnut" or bulbous annular sealing device.

The structure of the cuff 110 additionally includes one or more compressible parts, such as annular support parts 112, which act between the outer surface of the flexible tubing 102 and the cuff 110. When the cuff 110 is not inflated, the cuff 110 nonetheless occupies a certain volume, due to outward pressure from the support parts 112. Each support member 112 preferably comprises an annular foam plastic or foam rubber device, such as a disk or washer-shaped apparatus, having a central hole (not shown) through which the flexible tubing 102 passes. Each support member 112 preferably comprises a low or medium density plastic foam material with a thickness of between about 0.18 to 0.5 inches, so that the support parts 112 are sufficient to serve as a supporting partition within the cuff 110. Preferably, at least one of these support parts 112 is sized slightly larger in diameter than a human trachea for which the tracheal tube 100 is designed. However, due to the low or medium density of the material of which the support parts 112 are made, the parts 112 may be substantially compressed, without folding, while the tracheal tube 100 is being inserted into a patient's trachea.

The cuff 110 is self-inflating due to a number of features of the present invention. As shown in FIG. 2, for example, the first embodiment of the tracheal tube 100 includes one or more holes 200 in the portion of the flexible tubing 102 surrounded by the cuff 110. The relationship between the holes 200, cuff 110 and flexible tubing 102 is additionally shown in FIG. 3. During the inspiratory phase of positive pressure ventilation, the holes 200 permit the higher pressure air within the airway to flow into the cuff 110, thereby expanding the cuff 110 and increasing the effectiveness of the cuff's seal against the tracheal wall. This can more easily be seen with reference to FIG. 3A, illustrating a cross-sectional view of the tracheal tube 100 inserted into a patient's trachea. More particularly, FIG. 3A shows the cuff 110 in its fully inflated state, tightly sealing against the patient's trachea 300. For perspective, FIG. 3A also depicts a vertebra 302 the musculature 304 of the patient's neck and the skin 306 of the patient's neck.

As pressure within the airway decreases, decreasing the demand on the seal, pressure within the cuff 110 decreases simultaneously. Therefore, the cuff 110 automatically creates the appropriate seal, which dynamically corresponds to the rising and falling airway pressure occurring during each respiratory cycle. During the low pressure phase of ventilation, a low pressure static seal between the cuff 110 and the trachea 300 is maintained by one or more of the support parts 112. This low pressure static seal against the tracheal wall 300 facilitates normal blood flow in the tracheal tissues during the majority of the respiratory cycle.

Figure 4:
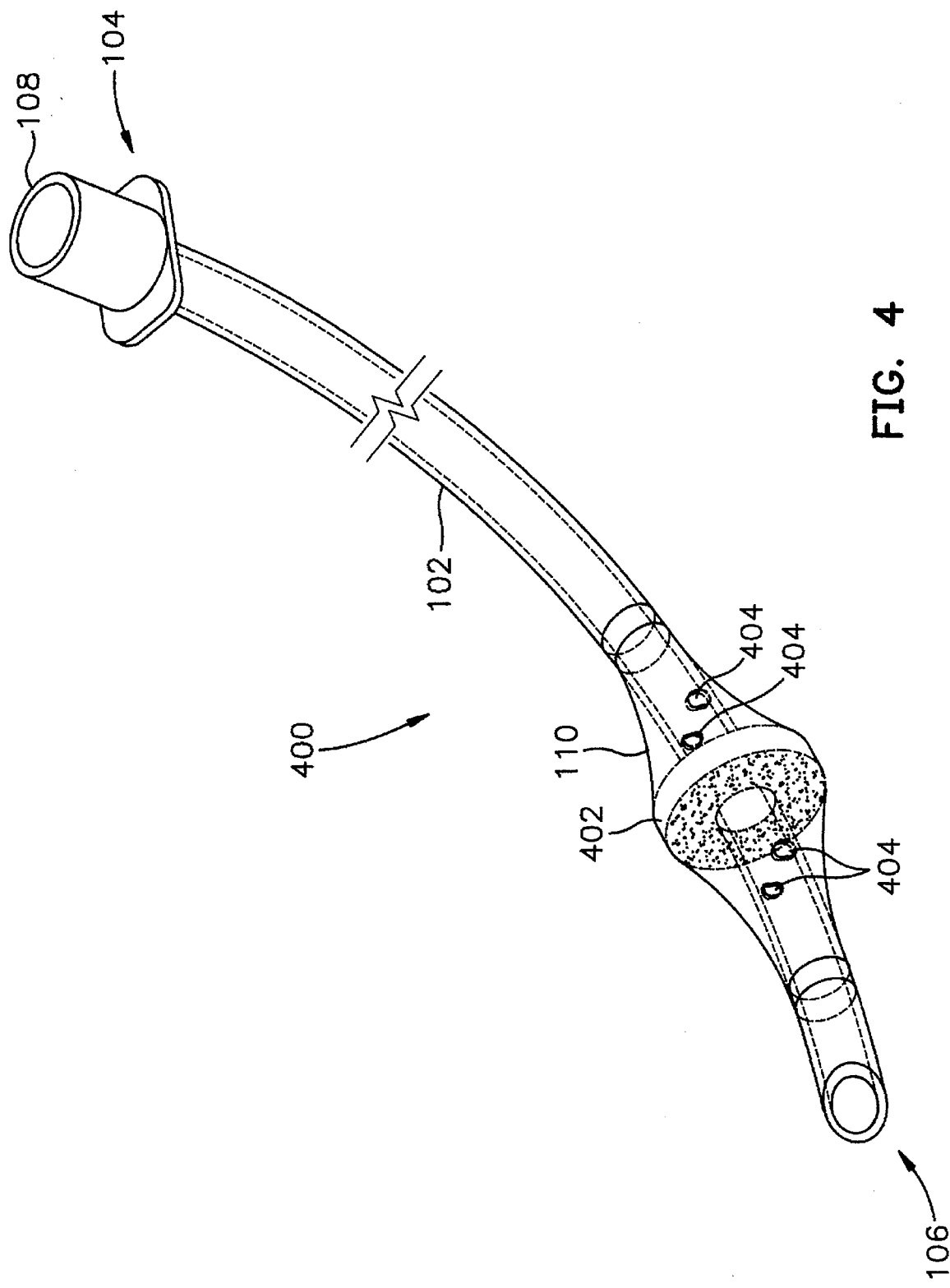
FIGS. 4 and 5A–5B show second and third embodiments respectively, of the invention exhibiting different disk and hole combinations.

FIG. 4 illustrates a tracheal tube 400, in accordance with a second embodiment of the present invention. The tracheal tube 400 includes a number of the components which are found in the tracheal tube 100, such as the flexible tubing 102, cuff 110, connector 108, and the proximal and distal ends 104 and 106. However, the cuff structure of the tracheal tube 400 differs from that of the tracheal tube 100 by utilizing only a single, flexible, compressible support part 402 which acts between the flexible tubing 102 and cuff 110. In this embodiment, holes 404 may be defined in the flexible tubing 102 on opposite ends of the support part 402, for example.

Figure 5:
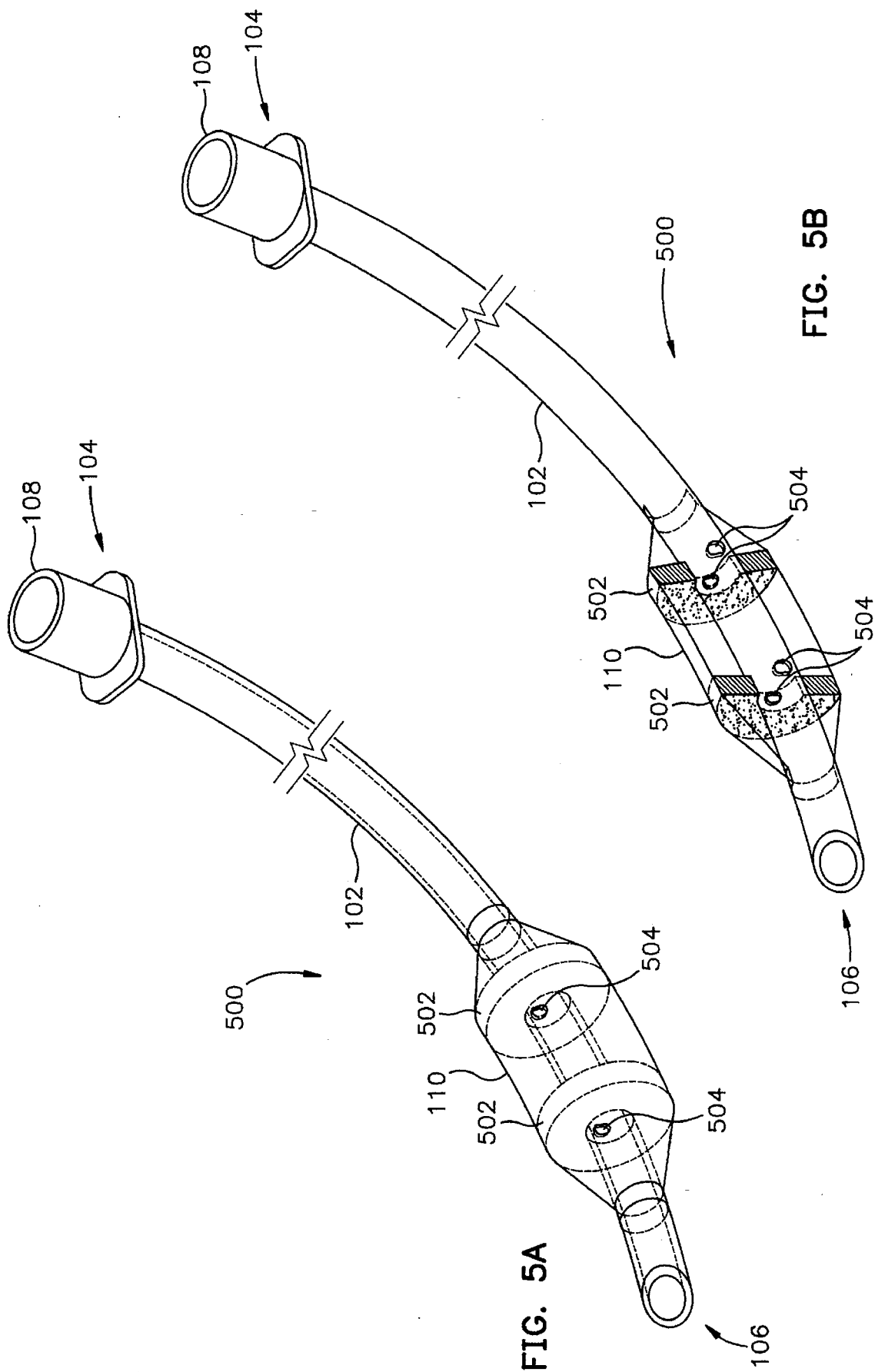

FIGS. 5A–5B depict a tracheal tube 500 in accordance with a third embodiment of the present invention. As shown in FIGS. 5A–5B, the tracheal tube 500 includes a number of components which are found in the tracheal tube 100 of FIG. 1. However, the cuff 110 includes two, rather than one, flexible, compressible supporting parts 502. In this embodiment, holes 504 are preferably defined in the flexible tubing 102 such that the holes 504 are covered by the support parts 502. In this configuration, air internal to the flexible tubing 102 is distributed through the holes 504 into pores of the support parts 502, which evenly disburse air within the cuff 110. This prevents potential uneven inflation of the cuff 110 along the length of the flexible tubing 102.

Figure 6:
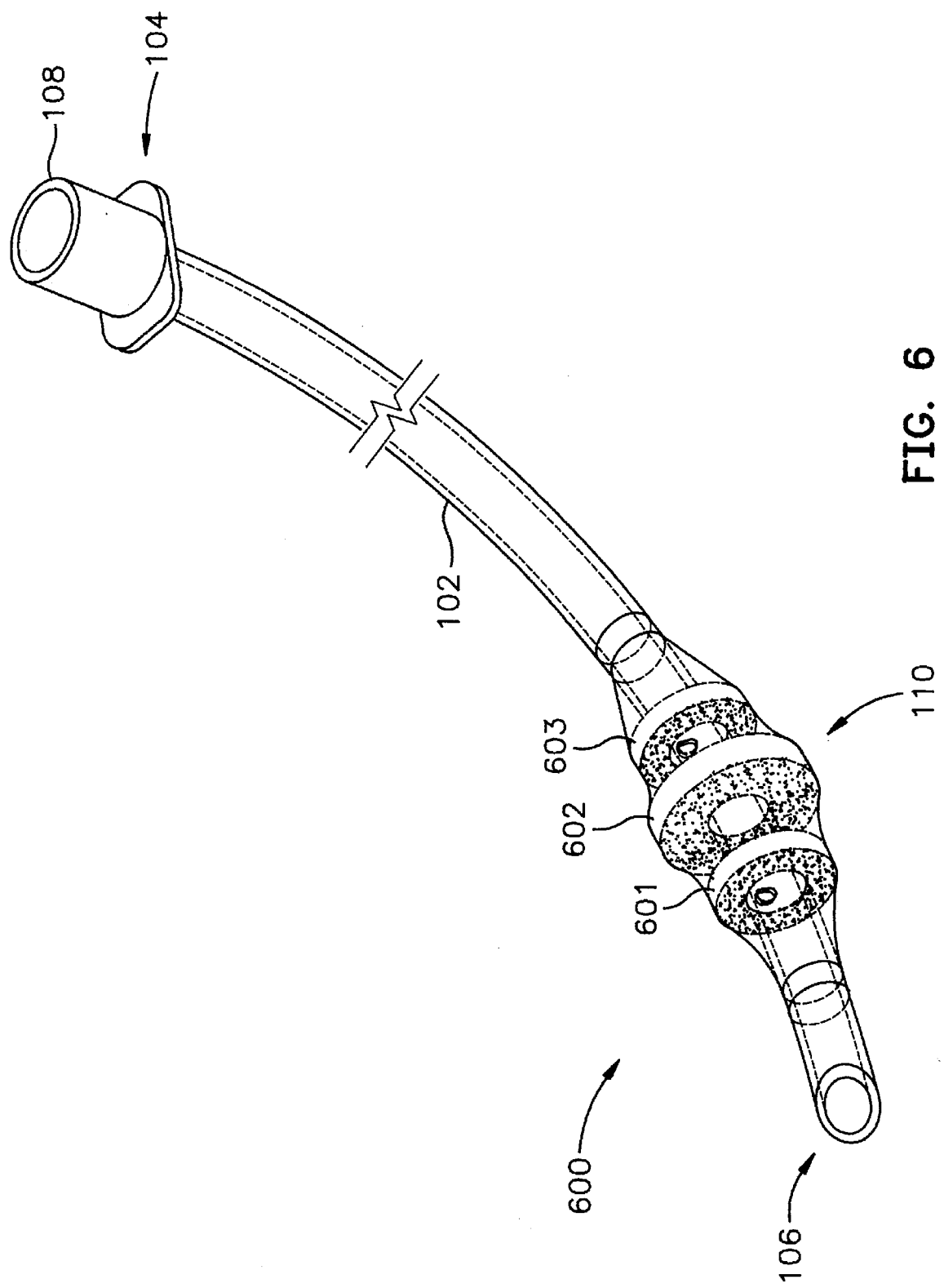
FIG. 6 is a perspective view of a fourth embodiment of the invention exhibiting different disk diameters.

FIG. 6 illustrates a tracheal tube 600 in accordance with a fourth embodiment of the invention. The tracheal tube 600 includes a number of components that are found in the first embodiment of the tracheal tube 100. However, the tracheal tube 600 includes flexible, compressible support parts 601–603 of varying sizes within the cuff 110. In this embodiment, the support parts 601-603 are preferably sized such that the proximal 603 and distal 601 support parts are smaller in diameter than the central support part 602. This effectively streamlines the cuff 110 when the cuff is not inflated, aiding in the insertion and removal of the tracheal tube 600 to and from the patient's trachea.

Figure 7:
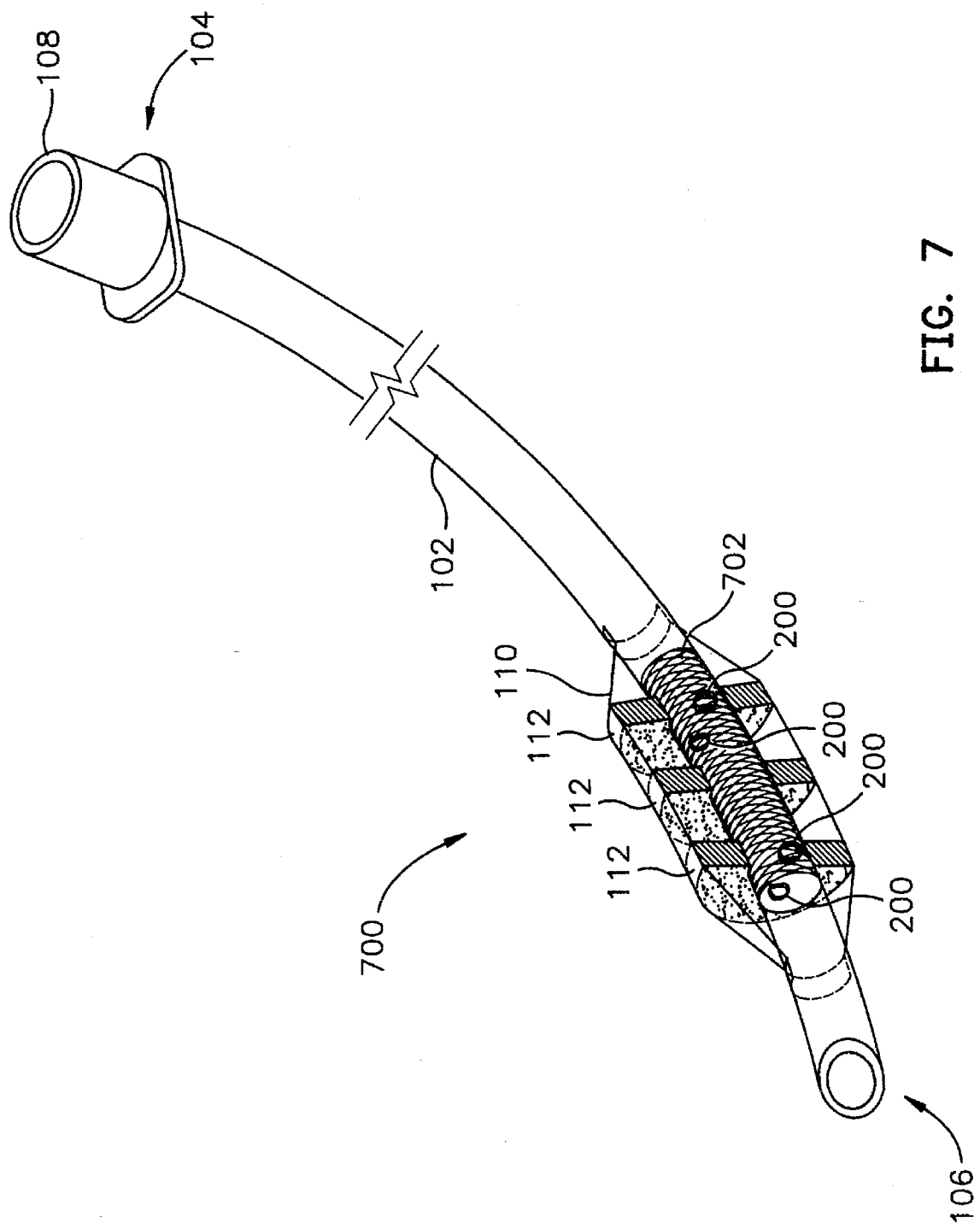
FIG. 7 is a cut-away perspective view of the first embodiment, showing a filter covering the passageways for communicating air pressure into the cuff.

FIG. 7 illustrates a tracheal tube 700, embodying a feature that is applicable to all embodiments of the present invention. The tracheal tube 700 includes a number of similar components that are found in the tracheal tube 100 of FIG. 1. However, the tracheal tube 700 includes a filter 702 covering the holes 200. The filter 702 preferably comprises a layer of porous or fibrous material, wrapped around or ensheathed about the flexible tubing 102. However, the filter 702 may instead be embodied in another arrangement, such as multiple mini-filters (not shown) individually disposed within the holes 200. The filter 702 prevents the passage of mucus or other foreign matter through the holes 200 and into the cuff 110. By preventing the introduction of foreign matter internal to the cuff 110, the filter 702 facilities the proper deflation of the cuff 110.

Figure 8:
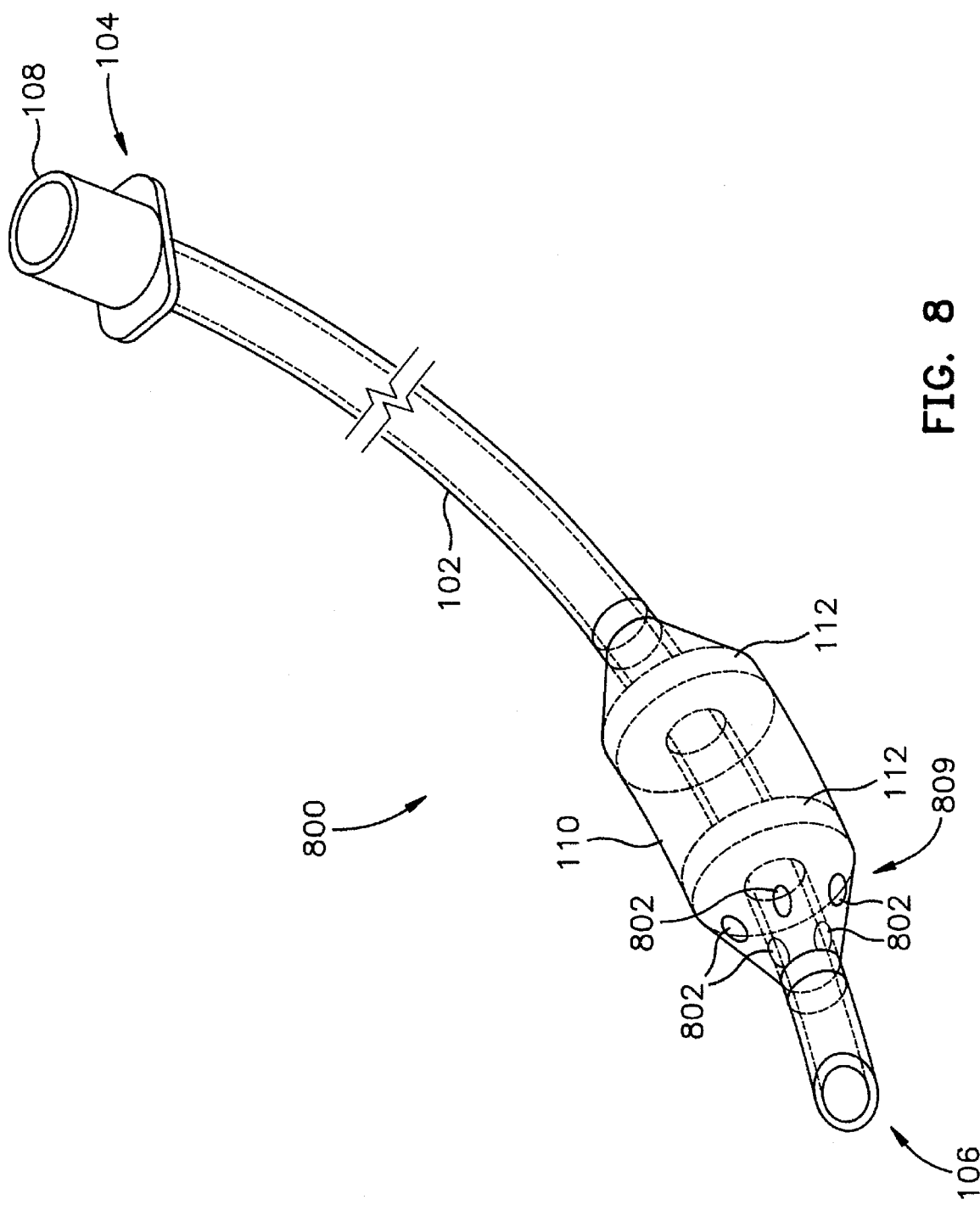
FIG. 8 is a perspective view of a fifth embodiment of the invention with passageways for communicating air pressure into the cuff being holes in the cuff itself.
Figure 9B:
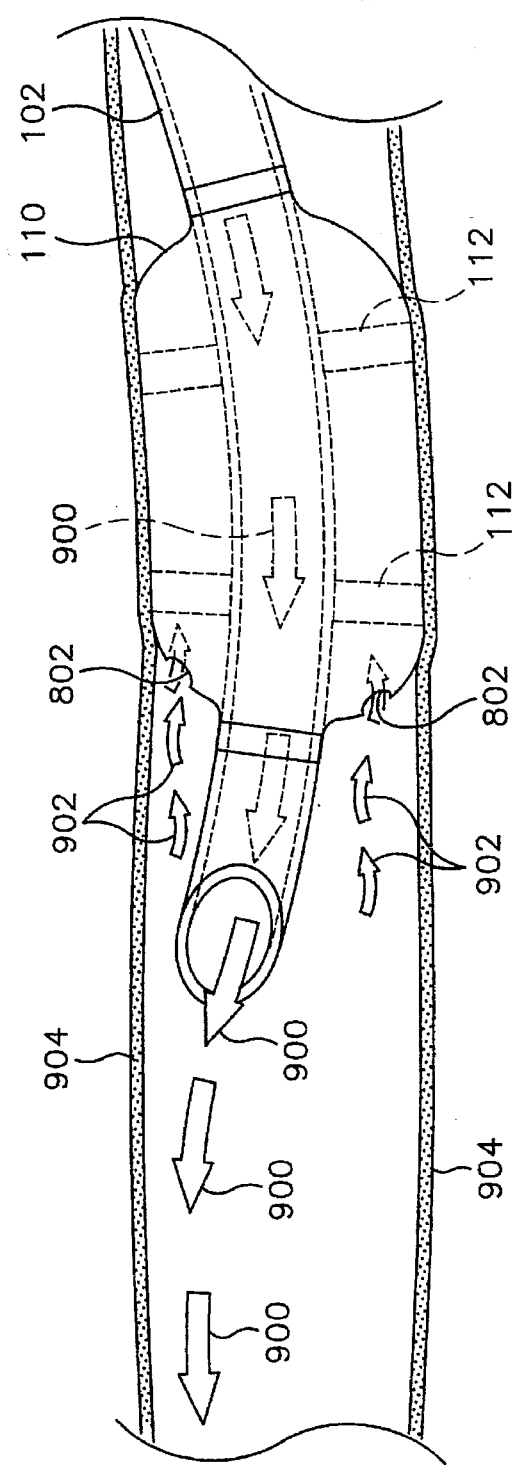

FIG. 8 illustrates a tracheal tube 800 in accordance with a fifth embodiment of the present invention. This embodiment includes a number of components that are found in the tracheal tube 100 (including, however, only two resilient, compressible support parts 112). However, the tracheal tube 800 lacks the holes 200, instead defining one or more holes 802 in a distal end 809 of an inflatable cuff 810. In this embodiment, the cuff 810 is not inflated by the pressure of air internal to the flexible tubing 102. Instead, the cuff 810 is inflated by back pressure in the lungs, created during the inspiratory phase of respiration. Nevertheless, as with the cuff 110, the pressure in the cuff 810 is substantially the same as the pressure in the trachea below the cuff 810; that is, as with all of the previous embodiments, there is at least one passage opening between the interior of the cuff and a space occupied by the distal end 106. More particularly, as pressure builds in the patient's lungs, air flows upward through the patient's trachea about the flexible tubing 102, and through the holes 802, thereby inflating the cuff 810. Therefore, the cuff 810 is automatically inflated during the phase of respiration where having a seal between the tracheal tube 800 and the trachea is most important. This is shown in greater detail in FIGS. 9A–9B. As shown in FIG. 9B, during the inspiratory phase of respiration, a stream of air flows through the flexible tubing 102 in the direction of the large arrows 900. The stream continues into the patient's lungs (not shown). Due to back pressure created in a patient's lungs, air begins to flow backward in a direction shown by small arrows 902. Accordingly, the backward flowing air flows through the holes 802, inflating the cuff 810 to seal against the patient's tracheal walls 904. During the expiratory cycle of respiration, the patient's lungs force air upward through the flexible tube 102 in a direction as shown by the large arrows 906 in FIG. 9A. At this point, the flexible tubing 102 permits the patient's lungs to freely move air in the direction 906. Accordingly, the pressure previously causing the flow of air in the direction 902 through the holes 802 is missing. And, as a result, a reverse air flow occurs through the holes 802 in a direction as shown by the small arrows 908.

In order to assure collapsibility of the support parts for easy and non-traumatic insertion through the vocal cords and trachea, without the need to draw a vacuum to collapse the parts, I have found that use of a low or medium density polymeric foam is desirable. The support parts may be made of such material. Relatedly, the greater the mass of the support parts, the less compressible they are. Thus, generally, it can be said that two disk-shaped support parts made from low density foam material exhibit a high compressibility, both in terms of the smallest circumference to which they can be compressed and in a minimal amount of force necessary to compress them. On the other hand, a three-disk or solid annular cylinder of foam material made of medium density foam compress down to relatively larger diameters in response to relatively higher radial forces than for the two-disk, low density support parts. Nevertheless, the selection of material is a design choice, and depends altogether upon the intended use.

Referring now to FIGS. 1, 2, 3, and 3A, method for tracheal ventilation according to my invention will be described. First, an opening to the trachea is exposed. This opening may be through a patient's mouth or nose, or by a hole opened directly through the patient's neck for a tracheostomy. Next, the distal end 106 of my tracheal tube 100 is inserted through the opening, without drawing a vacuum in the cuff to compress the support parts 112 in the cuff 110. The tracheal tube 100 is then advanced, distal end 106 first until the cuff 110 is totally within the trachea. There, a low pressure seal is formed between the trachea and the cuff 110 by the compressible, resilient support parts 112 which act between the outer surface of the tube 100 and the cuff 110. A ventilating pressure is introduced into the proximal end 104 which causes the patient's lungs to respire. In response to respiration of the patient's lungs, a varying pressure is introduced into the cuff 110 through the holes 200. The varying pressure varies the pressure of the seal between the cuff 110 and the trachea. After ventilation, the tracheal tube is removed by drawing it through the opening. This method may be practiced with all embodiments of my invention.

Clearly, although many embodiments have been described, other embodiments and modifications of the present invention will occur readily to those of ordinary skill in the art in view of these teachings. Therefore, this invention is to be limited only by the following claims, which include all such embodiments and modifications.

We claim:

1. A tracheal tube comprising:
   a tube having an outer surface, an inner surface, a proximal end and a distal end;
   a cuff mounted on the tube near the distal end;
   the cuff having:
      a flexible tubular cover with two edges disposed on the tube in surrounding relation thereto, and the edges secured to the outer surface of the tube to define a volume thereabout; and,
   one or more resilient support parts within the volume, each support part including an annulus surrounding the tube, the annulus being made of a resilient material; and
   one or more passageways for communicating airway pressure from a location proximate to said distal end, to the interior of the cuff.

2. The tracheal tube of claim 1, wherein a non-compressed volume of the resilient support parts is less than one-half of a volume defined by the cover.

3. The tracheal tube of claim 1, wherein at least one of the resilient support parts is a disk with an outer diameter greater than the diameter of a trachea in which the tracheal tube is to be inserted.

4. The tracheal tube of claim 1, wherein each resilient support part is a ring greater than 0.18 inches and less than 0.75 inches thick.

5. The tracheal tube of claim 1, wherein each resilient support part is made of a low-or medium-density polymeric foam.

6. The tracheal tube of claim 1, wherein each passageway includes:

a hole through the tube connecting the inner surface with the outer surface; and the hole being within the volume.

7. The tracheal tube of claim 6, wherein the hole is covered on the outer surface by an airflow filter.

8. The tracheal tube of claim 6, wherein the hole is covered on the outer surface by a resilient support part.

9. The tracheal tube of claim 1, wherein the tubular cover has an interior surface and an exterior surface, and each passageway of the one or more passageways comprises:

a hole through the cover connecting the interior surface with the exterior surface; and the hole is positioned near an edge of the cover proximate to the distal end.

10. The tracheal tube of claim 9, wherein the hole is covered on the interior surface by an airflow filter.

11. The tracheal tube of claim 9, wherein the hole is covered on the interior surface by a resilient support part.

12. A tracheal tube, comprising:

a flexible tubing with outer and inner surfaces and with proximal and distal ends;

an inflatable cuff mounted on the outer surface, near the distal end;

one or more passageways opening between an interior volume of the inflatable cuff and a space occupied by the distal end; and one or more resilient, compressible support parts in the interior volume defined by the inflatable cuff, acting between the outer surface and the inflatable cuff.

13. The tracheal tube of claim 12, wherein each resilient, compressible support part is an annular part and exerts a low sealing pressure on the inflatable cuff.

14. The tracheal tube of claim 12, wherein each resilient, compressible support part is a disk seated on the outer surface and exerts a low sealing pressure on the inflatable cuff.

15. The tracheal tube of claims 13 or 14, wherein the resilient, compressible support part is made of a low density foam material.

16. The tracheal tube of claim 12, wherein a passageway opens between the outer and inner surfaces.

17. The tracheal tube of claim 12, wherein a passageway opens through the inflatable cuff.

18. The tracheal tube of claim 12, wherein one or more resilient, compressible parts exert a low sealing pressure on the inflatable cuff.

19. The tracheal tube of claim 18, wherein a passageway opens between the outer and inner surfaces.

20. The tracheal tube of claim 18, wherein a passageway opens through the inflatable cuff.

21. A method of tracheal ventilation using a tracheal tube with distal and proximal ends, a self-inflating cuff mounted on the tracheal tube near the distal end, and one or more compressible, resilient support parts mounted on the tracheal tube, within the self-inflating cuff, the method comprising the steps of:

exposing an opening into a patient's trachea;

inserting the tracheal tube, distal end first through the opening; without drawing a vacuum in the self-inflating cuff to compress the support parts;

advancing the tracheal tube, distal end first, into the trachea until the self-inflating cuff is entirely within the trachea;

forming a low pressure seal between the trachea and the self-inflating cuff by action of the support parts; and ventilating lungs of the patient by introduction of a varying respiratory pressure through the proximal end.

* * * * *